US010420818B2

(12) United States Patent
Williams

(10) Patent No.: US 10,420,818 B2
(45) Date of Patent: Sep. 24, 2019

(54) METHODS OF TREATING INCONTINENCE AND OTHER SPHINCTER DEFICIENCY DISORDERS

(71) Applicant: Wake Forest University Health Sciences, Winston-Salem, NC (US)

(72) Inventor: James K. Williams, Clemmons, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 0 days.

(21) Appl. No.: 15/309,093

(22) PCT Filed: Apr. 30, 2015

(86) PCT No.: PCT/US2015/028490
§ 371 (c)(1),
(2) Date: Nov. 4, 2016

(87) PCT Pub. No.: WO2015/171417
PCT Pub. Date: Nov. 12, 2015

(65) Prior Publication Data
US 2017/0106050 A1 Apr. 20, 2017

Related U.S. Application Data

(60) Provisional application No. 61/990,190, filed on May 8, 2014.

(51) Int. Cl.
A61K 38/00 (2006.01)
A61K 38/19 (2006.01)
A61K 9/00 (2006.01)
A61K 38/39 (2006.01)
A61K 48/00 (2006.01)

(52) U.S. Cl.
CPC .......... *A61K 38/195* (2013.01); *A61K 9/0019* (2013.01); *A61K 9/0031* (2013.01); *A61K 9/0034* (2013.01); *A61K 38/39* (2013.01); *A61K 48/005* (2013.01)

(58) Field of Classification Search
None
See application file for complete search history.

(56) References Cited

U.S. PATENT DOCUMENTS

| 5,385,561 | A | 1/1995 | Cerny |
| 5,588,960 | A | 12/1996 | Edwards et al. |
| 5,925,629 | A | 7/1999 | Place |
| 6,761,908 | B1 * | 7/2004 | Roreger ............... A61K 9/19 424/484 |
| 7,015,253 | B2 | 3/2006 | Escandon et al. |
| 7,598,028 | B2 | 10/2009 | Macoska |
| 7,662,392 | B2 | 2/2010 | Itescu |
| 7,939,057 | B2 | 5/2011 | Battista et al. |
| 8,435,953 | B2 | 5/2013 | Tabata |
| 8,513,007 | B2 | 8/2013 | Penn et al. |
| 8,513,213 | B2 | 8/2013 | Penn et al. |
| 2008/0311219 | A1 | 12/2008 | Gosiewska et al. |
| 2010/0003297 | A1 | 1/2010 | Tobias et al. |
| 2010/0272679 | A1 * | 10/2010 | Penn .................... C07K 14/522 424/85.2 |
| 2011/0081323 | A1 | 4/2011 | Kleinsek et al. |
| 2017/0106050 | A1 | 4/2017 | Williams |

FOREIGN PATENT DOCUMENTS

| JP | S63-063624 | 3/1988 |
| WO | WO 2006/032075 | 3/2006 |
| WO | 2007/035843 | 3/2007 |

OTHER PUBLICATIONS

Ching-Shwun and Lue, Stem Cell Therapy for Stress Urinary Incontinence: A Critical Review; Stem Cells and Development, vol. 21, No. 6, 2012.*
Chen FM et al. "Homing of endogenous stem/progenitor cells for in situ tissue regeneration: Promises, strategies, and translational perspectives" *Biomaterials* 32: 3189-3209 (2011).
Chen J et al. "Simultaneous regeneration of articular cartilage and subchondral bone in vivo using MSCs induced by a spatially controlled gene delivery system in bilayered integrated scaffolds" Biomaterials 32, 4793-4805 (2011).
D'Apuzzo et al. "The chemokine SDF-1, stromal cell-derived factor 1, attracts early stage B cell precursors via the chemokine receptor CXCR4" Eur. J. Immunol. vol. 27, 1788-1793 (1997).
Eman RM et al. "Stromal Cell-Derived Factor-1 Stimulates Cell Recruitment, Vascularization and Osteogenic Differentiation" *Tissue Eng Part A.* 20(3-4), 466-73 ( 2013).
Ghadge SK et al. "SDF-1a as a therapeutic stem cell homing factor in myocardial infarction" *Pharmacol Ther.* 129(1), 97-108 (2011).
Hisada M et al. "Successful transplantation of reduced-sized rat alcoholic fatty livers made possible by mobilization of host stem cells", Am J Transplant. Dec. 2012;12(12):3246-56.
Huang P et al. "New strategies for improving stem cell therapy in ischemic heart disease" *Heart Fail Rev.* 21:737-752 [Epub ahead of print] (2016).
Kim DH et al. "Enhancing neurogenesis and angiogenesis with target delivery of stromal cell derived factor-1α using a dual ionic pH-sensitive copolymer" *Biomaterials.* 61, 115-25 (2015).
Liu H et al. "Local administration of stromal cell-derived factor-1 promotes stem cell recruitment and bone regeneration in a rat periodontal bone defect model" Mater Sci Eng C Mater Biol Appl. Aug. 2015;53:83-94.
Iohara K et al. "Complete pulp regeneration after pulpectomy by transplantation of CD105+ stem cells with stromal cell-derived factor-1" Tissue Eng Part A. 17(15-16), 1911-20 (2011).
Macarthur JW et al. "Preclinical evaluation of the engineered stem cell chemokine stromal cell-derived factor 1α analog in a translational ovine myocardial infarction model" *Circ Res.* 114(4), 650-9 (2014).
Maeshima A et al. "Regenerative medicine for the kidney: renotropic factors, renal stem/progenitor cells, and stem cell therapy" *Biomed Res Int.* 595493. Epub (2014).

(Continued)

*Primary Examiner* — Jeanette M Lieb
(74) *Attorney, Agent, or Firm* — Myers Bigel, P.A.

(57) ABSTRACT

A method of treating a sphincter deficiency disorder (e.g., incontinence; gastrointestinal disorders) is carried out by administering stromal cell-derived factor 1 (SDF-1) to a sphincter or sphincter complex, such as a urethral or gastrointestinal sphincter (e.g., a rectal sphincter) of the subject in a treatment-effective amount.

18 Claims, 1 Drawing Sheet

(56) References Cited

OTHER PUBLICATIONS

Ohnishi H, et al. "Stromal cell-derived factor-1 (SDF1)-dependent recruitment of bone marrow-derived renal endothelium-like cells in a mouse model of acute kidney injury", *J Vet Med Sci.* 77(3), 313-9 (2015).
Rabbany SY et al. "Continuous delivery of stromal cell-derived factor-1 from alginate scaffolds accelerates wound healing" *Cell Transplant.* 19(4), 399-408 (2010).
Raghavan et al. "Successful Implantation of Bioengineered, Intrinsically Innervated, Human Internal Anal Sphincter", Gastroenterology, 141, 310-319 (2011).
Schuh A et al. "Myocardial regeneration by transplantation of modified endothelial progenitor cells expressing SDF-1 in a rat model" *J Cell Mol Med.* 16(10), 2311-20 (2012).
Schuh A et al. "Effect of SDF-1 α on Endogenous Mobilized and Transplanted Stem Cells in Regeneration after Myocardial Infarction" *Curr Pharm Des.* [Epub ahead of print] (2013); 20:1964-1970 (2014).
Song M et al. "Regeneration of chronic myocardial infarction by injectable hydrogels containing stem cell homing factor SDF-1 and angiogenic peptide Ac-SDKP" *Biomaterials.* 35(8), 2436-45 (2014).
Tang JM et al. "VEGF/SDF-1 promotes cardiac stem cell mobilization and myocardial repair in the infarcted heart" *Cardiovasc Res.* 91(3), 402-11 (2011).
Williams JK et al. "Cell vs. Chemokine Therapy in a Nonhuman Primate Model of Chronic Intrinsic Urinary Sphincter Deficiency" *J Urol.* 196(6):1809-1815. Dec. 2016.
Woo LL et al. "Over expression of stem cell homing cytokines in urogenital organs following vaginal distention", *J Urol.* 177(4), 1568-72 (2007).
Yu J, et al. "The effect of stromal cell-derived factor-1α/heparin coating of biodegradable vascular grafts on the recruitment of both endothelial and smooth muscle progenitor cells for accelerated regeneration" *Biomaterials.* 2012 33(32), 8062-74 (2012).
Zambon JP et al. "Kidney regeneration: Where we are and future perspectives" *World J Nephrol.* 3(3), (2014).
Zhang W et al. "The use of type 1 collagen scaffold containing stromal cell-derived factor-1 to create a matrix environment conducive to partial-thickness cartilage defects repair" Biomaterials 2013; 34: 713-723.
Zisa D et al. "Intramuscular VEGF activates an SOF1-dependent progenitor cell cascade and an SOF1-independent muscle paracrine cascade for cardiac repair" *Am J Physiol Heart Circ Physiol* 6: 2422-243 (2011).
International Preliminary Report on Patentability Corresponding to International Application No. PCT/US2015/028490; dated Nov. 17, 2016; 8 Pages.
Notification of Transmittal of the International Search Report and the Written Opinion of the International Searching Authority, or the Declaration, PCT/US2015/028490, dated Jul. 24, 2015.
Heinrich Schulte-Baukloh et al. "Botulinum—A Toxin Detrusor and Sphincter Injection in Treatment of Overactive Bladder Syndrome: Objective Outcome and Patent Satisfaction" *European Urology,* 48(6), pp. 984-990, 2005.
MM Koraitim "The male urethral sphincter complex revisited: an anatomical concept and its physiological correlate" *Journal of Urology,* 179(5), pp. 1683-1689, 2008.
Sender Herschorn "Current Use of Injectable Agents for Female Stress Urinary Incontinence" *Reviews in Urology,* 7(1), pp. S12-S21, 2005.
Supplementary European Search Report corresponding to European Patent Application No. 15789938, dated Oct. 27, 2017, 8 pages.
Costello, C. M., et al., "A role for the CXCL12 receptor, CXCR7, in the pathogenesis of human pulmonary vascular disease." Eur Respir J 2012; 39: 1415-1424.
Wang, J., and Knaut, H. "Chemokine signaling in development and disease." Development; Nov. 15, 2014; 141(22): 4199-4205.
Karpova, D., and Bonig, H. "Concise Review: CXCR4/CXCL12 Signaling in Immature Hematopoiesis—Lessons From Pharmacological and Genetic Models." Stem Cells; 2015;33:2391-2399.
Avniel, S., et al., "Involvement of the CXCL12/CXCR4 Pathway in the Recovery of Skin Following Burns." J. Investigative Dermatology; 2006; vol. 126: 468-475.
Werner, L., Guzner-Gur H., and Dotan, I. "Involvement of CXCR4/CXCR7/CXCL12 Interactions in Inflammatory Bowel Disease." Theranostics; 2013; vol. 3, Issue 1, 40-46.
De Paepe, B., et al.,"Upregulation of chemokines and their receptors in Duchenne muscular dystrophy: potential for attenuation of myofiber necrosis." Muscle & Nerve; Dec. 2012; 917-925.
Mehta, N. N., et al., "Higher plasma CXCL12 levels predict incident myocardial infarction and death in chronic kidney disease: findings from the Chronic Renal Insufficiency Cohort study." European Heart Journal; 2014; 35; 2115-2122.
Darisipudi, M. N., et al., "Dual Blockade of the Homeostatic Chemokine CXCL12 and the Proinflammatory Chemokine CCL2 Has Additive Protective Effects on Diabetic Kidney Disease." The American Journal of Pathology, vol. 179, No. 1, Jul. 2011; 116-124.
Machelon, V., et al., "CXCL12 expression by healthy and malignant ovarian epithelial cells." BMC Cancer; 2011; 11:97.
Cojoc, M., et al., "Emerging targets in cancer management: role of the CXCL12/CXCR4 axis." OncoTargets and Therapy; 2013;6: 1347-1361.
Shu, H-K. G., et al., "Inhibition of the CXCL12/CXCR4-Axis as Preventive Therapy for Radiation-Induced Pulmonary Fibrosis." Plos One; Nov. 7, 2013; 8(11): e79768.
Hoh, B.L., et al., "Stromal cell-derived factor-1 promoted angiogenesis and inflammatory cell infiltration in aneurysm walls." J Neurosurg; vol. 120; Jan. 2014; 73-86.
Badra, S., et al., "A Nonhuman Primate Model of Stable Urinary Sphincter Deficiency." The Journal of Urology; May 2013; vol. 189; 1967-1974.
Badra, S., et al., "Long-Term Structural and Functional Effects of Autologous Muscle Precursor Cell Therapy in a Nonhuman Primate Model of Urinary Sphincter Deficiency." The Journal of Urology., Nov. 2013; vol. 190; 1938-1945.
Williams, J.K. et al., "Efficacy and initial safety profile of CXCL12 treatment in a rodent model of urinary sphincter deficiency." Stem Cells Trans Med; Aug. 2017;6(8):1740-1746.
Williams, J.K. et al., "Cell versus chemokine therapy in a nonhuman primate model of chronic intrinsic urinary sphincter deficiency." J. Urol. Dec. 2016; 196(6):1809-1815.
Mangir, "Stem Cell Therapies in Post-Prostatectomy Erectile Dysfunction: A Critical Review" The Canadian Journal of Urology, 24(1):8609-8619 (2017).
Williams, J.K. et al. "Long-term efficacy of cell therapy in a nonhuman primate model of stable urinary sphincter deficiency" Neurourology Urodynamics, 32(6):835-836 (2013) Abstract 224.
Mitterberger et al. "Myoblast and Fibroblast Therapy for Post-Prostatectomy Urinary Incontinence: 1-Year Followup of 63 Patients" The Journal of Urology, 179:226-231 (2008).
Office Action issued for corresponding Japanese Patent Application No. 2016-566943 (6 pages) (dated Jan. 16, 2019).

\* cited by examiner

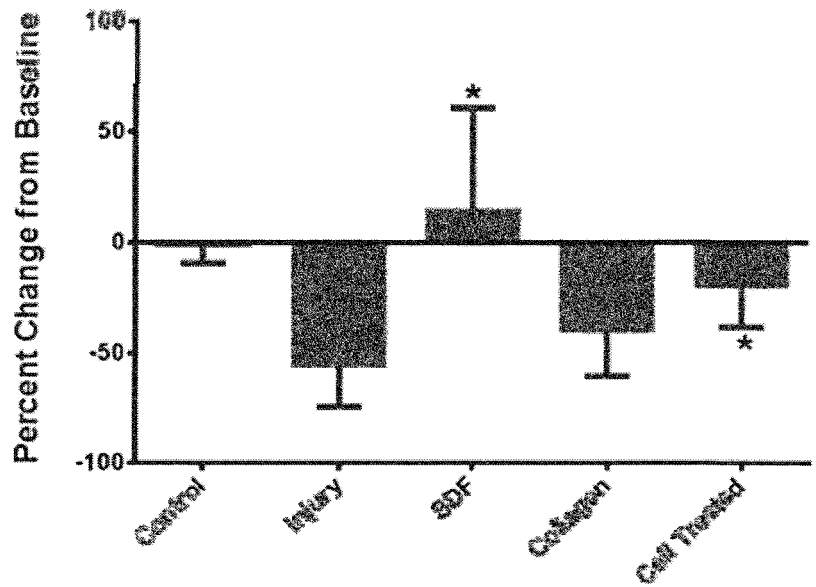
Figure 1A: Percent Change of MUP for Each Group at Six Months Post Treatment/Injury
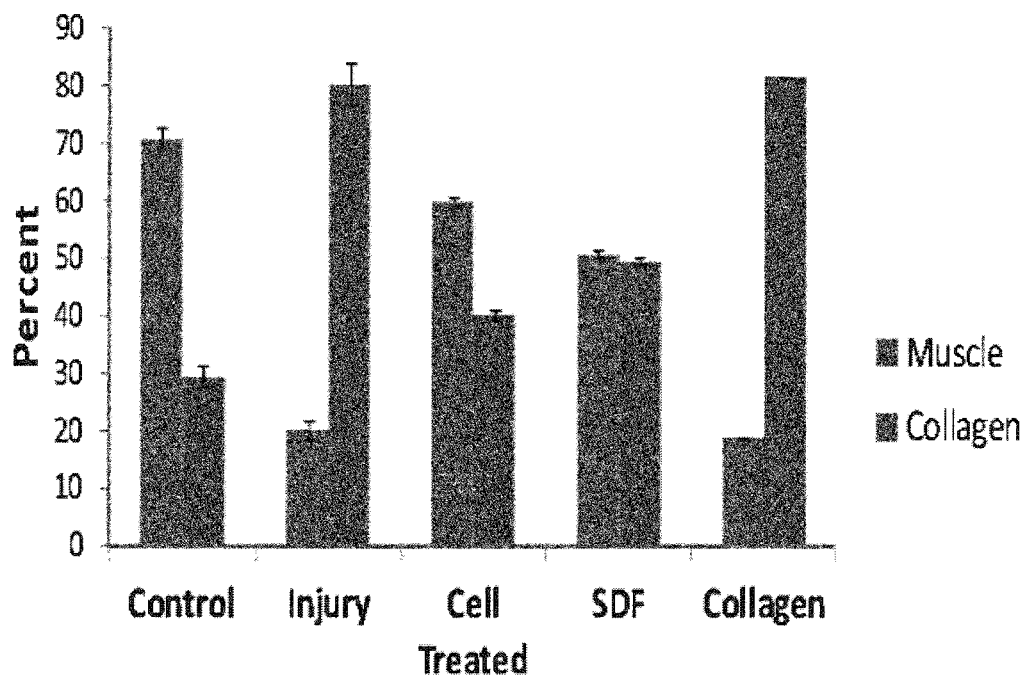
Figure 1B Muscle and Collagen Content Six Months Post Treatment/Injury

METHODS OF TREATING INCONTINENCE AND OTHER SPHINCTER DEFICIENCY DISORDERS

RELATED APPLICATIONS

This application is a 35 U.S.C. § 371 national phase entry of PCT Application PCT/US2015/028490, filed Apr. 30, 2015, and published in English on Nov. 12, 2015, as International Publication No. WO 2015/171417, and which claims the benefit of U.S. Provisional Application Ser. No. 61/990,190, filed May 8, 2014, the disclosure of each of which is incorporated by reference herein in its entirety.

BACKGROUND OF THE INVENTION

Sphincter deficiency disorders such as incontinence, including persistent urinary and bowel incontinence, is associated with significant impairment of quality of life, social isolation and depressive symptoms. The underlying pathology is not always well understood, but is generally associated with damage to the innervation of the muscle and/or age-related loss of sphincter muscle cells.

Treatments for such sphincter deficiencies are not adequate and alternatives are needed. This has led to consideration of cell therapy to support regeneration of the damaged muscle as well as re-establish tissue supporting innervation and vascularization. Preclinical and clinical studies support short-term efficacy of this therapy. However, autologous cell therapy requires biopsy and lengthy cell expansion protocols. Additionally, it is unclear if cells remain at the site of injection in sufficient numbers to constitute the bulk of the regenerated tissue. Accordingly, new approaches to the treatment of incontinence and other sphincter deficiency disorders are needed.

SUMMARY OF THE INVENTION

A first aspect of the invention is a method of treating a sphincter deficiency disorder (e.g., incontinence; gastrointestinal disorders) in a subject in need thereof, comprising administering stromal cell-derived factor 1 (SDF-1) to a sphincter or sphincter complex, such as a urethral or gastrointestinal sphincter (e.g., a rectal sphincter) of the subject in a treatment-effective amount.

In some embodiments, the disorder is a gastrointestinal disorder and the sphincter is a gastrointestinal sphincter.

In some embodiments the disorder is urinary incontinence and said sphincter is a urethral sphincter; in other embodiments the disorder is bowel incontinence (also referred to as "fecal incontinence") and said sphincter is a rectal sphincter.

In some embodiments, the sphincter comprises smooth muscle; in some embodiments, the sphincter comprises skeletal muscle. In some embodiments, the sphincter comprises a complex of both smooth and skeletal muscle (e.g., the urethral sphincter, an esophageal sphincter, the pyloric sphincter, the ileocecal sphincter). In some embodiments, the administering step is carried out by injecting SDF-1 into the sphincter or sphincter complex, for example at a plurality of sites within the sphincter or sphincter complex (e.g., in or adjacent the junction between the skeletal muscle layer and the smooth muscle layer of a sphincter complex).

A further aspect of the invention is a sterile injectable composition useful for the treatment of a sphincter deficiency disorder, comprising: SDF-1 in a treatment effective amount, optionally a viscosity-enhancing agent such as collagen (e.g., in an amount sufficient to inhibit flow of the composition away from the injection site), and an aqueous carrier (e.g., physiological saline solution).

BRIEF DESCRIPTION OF THE DRAWINGS

FIG. 1A. Maximal urethral pressure (MUP) values (% change from baseline) 6 months post injection in uninjured controls, injured (no cells), cell treated, SDF-1 (CXCL-12), or collagen treated monkeys.

FIG. 1B. Sphincteric muscle and collagen content (% of sphincter area) in the same animals as described in connection with FIG. 1A.

DETAILED DESCRIPTION OF PREFERRED EMBODIMENTS

The present invention is primarily concerned with the treatment of human subjects, but the invention may also be carried out on animal subjects, particularly mammalian subjects such as dogs, cats, livestock and horses for veterinary purposes. Subjects may be male or female. While subjects may be of any suitable age, the subjects are in some embodiments neonatal, infant, juvenile, adolescent, adult, or geriatric subjects.

"Treat" as used herein refers to any type of treatment that imparts a benefit to a patient, particularly reducing or ameliorating severity of a symptom as described herein, delaying or retarding progression or worsening of a symptom or disorder as described herein, etc.

"Gastrointestinal sphincter" as used herein includes the upper esophageal sphincter, the lower esophageal sphincter, the pyloric sphincter, the ileocecal sphincter, the sphincter of Oddi (or Glisson's sphincter), and the rectal sphincter (including the internal and external anal sphincters). The lower esophageal sphincter is sometimes referred to as the "cardiac" sphincter, but this refers to its location and not the type of muscle tissue from which it is formed.

"Gastrointestinal disorder" as used herein includes, but is not limited to, acid reflux, gastroesophageal reflux (or "GERD"), laryngpharyngeal reflux (LPR or "silent reflux"), sphincter of Oddi dysfunction, gastrointestinal motility disorders (e.g., gastroparesis; GERD as noted above; fecal incontinence as discussed below), etc.

"Incontinence" as described herein is, in general, latchkey or urge incontinence, or persistent incontinence, which may arise from any of a variety of causes or conditions. Examples of causes or conditions leading to incontinence (some but not all of which cause damage to the sphincter muscle) which may be treated by the methods and compositions described herein include, but are not limited to, for urinary incontinence: pregnancy and childbirth, aging, hysterectomy, painful bladder syndrome, prostatitis, enlarged prostate, prostate cancer, bladder cancer, bladder stones, cancer treatment (e.g., cancer chemotherapy or radiation therapy of the pelvic region), multiple sclerosis, neurological disorders (e.g., Parkinson's disease, stroke, brain tumor or spinal injury, etc.) idiopathic muscle weakness, etc., and for bowel or fecal incontinence: muscle damage (e.g., caused by chronic constipation, during childbirth (particularly arising from an episiotomy), surgery (e.g., hemorrhoid surgery), rectal prolapse, chemotherapy or radiation therapy of the pelvic region, etc.), nerve damage (e.g., caused by childbirth, chronic constipation or constant straining during bowel movement, spinal cord injury, stroke, diabetes, multiple sclerosis, surgery (e.g., Hemorrhoid surgery), rectal prolapse, cancer chemotherapy or radiation therapy of the pelvic region, etc.), loss of storage capacity in the rectum (e.g., due to scar formation from surgery, radiation, treatment, inflammatory bowel disease, etc.), etc.

"Pharmaceutically acceptable" as used herein means that the compound or composition is suitable for administration to a subject to achieve the treatments described herein, without unduly deleterious side effects in light of the severity of the disease and necessity of the treatment.

"Concurrently" as used herein means sufficiently close in time to produce a combined effect (that is, concurrently may be simultaneously, or it may be two or more events occurring within a short time period before or after each other).

1. Active Compounds.

The active compound used herein is the chemokine protein stromal cell-derived factor 1 (SDF-1). The compound is also known as the C-X-C motif chemokine 12 (CXCL12), as in humans it is encoded by the CXCL12 gene. SDF-1 is known and described in, for example, M. D'Apuzzo et al., The chemokine SDF-1, stromal cell-derived factor 1, attracts early stage B cell precursors via the chemokine receptor CXCR4, *Eur. J. Immunol.* 27, 1788-1793 (1997); Y. Tabata, U.S. Pat. No. 8,435,953, and Penn et al., U.S. Pat. Nos. 8,513,213 and 8,513,007; and S. Itescu, U.S. Pat. No. 7,662,392, the disclosures of which are incorporated by reference herein in their entirety.

As used herein, SDF-1 may include isoforms and mature forms thereof such as SDF-1.beta., SDF-1 gamma, SDF-1delta, SDF-1epsilon and SDF-1phi in addition to SDF-1alpha or a mature form thereof, or a mixture thereof in an arbitrary ratio or the like. SDF-1 preferred in the present invention includes SDF-1alpha, SDF-1beta, a mixture thereof in an arbitrary ratio or the like. See U.S. Pat. No. 8,435,953.

In the present invention, as long as SDF-1 has activity as a chemokine, SDF-1 may be substituted, deleted and/or added by one or plural amino acid(s) in the amino acid sequence. Similarly, it may be substituted, deleted and/or added by sugar chain. SDF-1 may form a salt (preferably, an acid addition salt) with a physiologically acceptable acid (for example, an inorganic acid or an organic acid) or a base (for example, an alkali metal salt). Examples of the salt include a salt with an inorganic acid (for example, hydrochloric acid, phosphoric acid, hydrobromic acid, or sulfuric acid) and a salt with an organic acid (for example, acetic acid, formic acid, propionic acid, fumaric acid, maleic acid, succinic acid, tartaric acid, citric acid, malic acid, oxalic acid, benzoic acid, methanesulfonic acid, or benzenesulfonic acid). See Id.

The type of SDF-1 is not limited in the present invention. SDF-1 used in the present invention may be derived from mammals such as human, or non-human animals such as monkey, sheep, cow, horse, pig, dog, cat, rabbit, rat, or mouse. Normally, target species may be selected for application of "a sustained release composition containing (1) SDF-1 and (2) a hydrogel containing modified gelatin having a carboxyl group and/or a sulfo group" as disclosed in the present invention (hereafter may be sometimes abbreviated to the "composition of the present invention"). For example, when the composition of the present invention is applied to human, the composition of the present invention may be produced using human SDF-1 (for example, SDF-1alpha (GeneBank Accession No. NP954637) or SDF-1beta (GeneBank Accession No. NP000600)). See Id.

In the present invention, SDF-1 may be purified to a level at which the action of SDF-1 is not inhibited by other contaminants. Preferably, SDF-1 may be purified to be usable as a pharmaceutical preparation. See Id.

In the present invention, SDF-1 may be obtained from natural sources or produced by a genetic engineering technique. When obtained from natural sources, SDF-1 may be extracted from various organs such as the spleen of mammals such as human or non-human animal (for example, monkey, sheep, cow, horse, dog, cat, rabbit, rat, or mouse), in which SDF-1 is already known to exist. To give a specific example of an organ in which SDF-1 is known to exist, for example, SDF-1 is known to be present in a large amount in organs in which tumor cells expressing CXCR4, a SDF-1 receptor, transfer with high frequency. On the other hand, when produced by a genetic engineering technique, a gene coding SDF-1 from a mammal such as human or non-human animals (for example, monkey, sheep, cow, horse, pig, dog, cat, rabbit, rat, or mouse) is incorporated into a suitable vector, which is introduced into a suitable host cell for transformation, to thereby be able to obtain the target recombinant SDF-1 from a culture supernatant of the transformant. The host cell herein is not limited and various host cells such as *E. coli*, yeast cells, various insect cells such as silkworm cells and various animal cells, which have been normally used in the genetic engineering techniques, may be used. See Id.

The active compounds disclosed herein can, as noted above, be prepared in the form of their pharmaceutically acceptable salts. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; (b) salts formed from elemental anions such as chlorine, bromine, and iodine, and (c) salts derived from bases, such as ammonium salts, alkali metal salts such as those of sodium and potassium, alkaline earth metal salts such as those of calcium and magnesium, and salts with organic bases such as dicyclohexylamine and N-methyl-D-glucamine.

The SDF-1 may be administered directly, e.g., by injection, or by administering (e.g., by injection) a nucleic acid vector (e.g., integrating and non-integrating viral vectors, retroviral vectors, plasmid vectors, linear DNA vectors, etc.) that encodes SDF-1 and expresses (e.g., transiently or constitutively expresses) SDF-1 in the patient's tissue. In general such vectors comprise a nucleic acid segment encoding SDF-1 as described above operatively associated with a promoter (e.g., a CMV promoter) that is operable in the subject's tissue. Suitable vectors, including plasmid vectors, are known or will be apparent to those skilled in the art based on the present disclosure and include but are not limited to the plasmid deposited with the American Type Culture Collection under accession number PTA-13320, as described in, for example, Penn et al., U.S. Pat. Nos. 8,513,213 and 8,513,007, the disclosures of which are incorporated by reference herein in their entirety.

Where a subject is receiving an internal sphincter implant, such as an internal anal sphincter implant as described in S. Raghavan et al., *Gastroenterology* 141, 310-319 (2011), the present invention may be carried out by administering the SDF-1 ex vivo into the tissue construct prior to implantation, with the tissue construct then implanted, carrying into the patient the SDF-1 in an amount effective to achieve the results described herein, preferably with respect to both the internal (smooth muscle) and external (skeletal muscle) portions of the sphincter complex.

2. Pharmaceutical Formulations.

The active compounds described above may be formulated for administration in a pharmaceutical carrier in accordance with known techniques. See, e.g., Remington, *The Science And Practice of Pharmacy* ($9^{th}$Ed. 1995). In the manufacture of a pharmaceutical formulation according to the invention, the active compound (including the physiologically acceptable salts thereof) is typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.01 or 0.5% to 95% or 99% by weight of the active compound. One or more active compounds may be incorporated in the formulations of the invention, which may be prepared by any of the well known techniques of pharmacy comprising admixing the components, optionally including one or more accessory ingredients.

Formulations of the present invention suitable for parenteral administration comprise sterile aqueous and non-aqueous injection solutions of the active compound(s), which preparations are preferably isotonic with the blood of the intended recipient. These preparations may contain antioxidants, buffers, bacteriostats and solutes which render the formulation isotonic with the blood of the intended recipient. Aqueous and non-aqueous sterile suspensions may include suspending agents and thickening agents. The formulations may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, in one aspect of the present invention, there is provided an injectable, stable, sterile composition comprising an active compound(s), or a salt thereof, in a unit dosage form in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

In addition to active compound(s), the pharmaceutical compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well known in the art.

3. Dosage and Routes of Administration.

As noted above, the present invention provides pharmaceutical formulations comprising the active compounds (including the pharmaceutically acceptable salts thereof), in pharmaceutically acceptable carriers for parenteral administration (particularly intramuscular or intra-sphincter complex injection, such as by translumenal injection).

Translumenal injection (e.g., transurethral or trans-rectal injection) may be carried out by any suitable technique, including but not limited to those described in U.S. Pat. Nos. 7,015,253; 5,925,629; 5,588,960; and 5,385,561, and US Patent Application Publication No. US2010/0003297A1 by Tobias et al. (MIT), the disclosures of which are incorporated herein by reference in their entirety.

The pharmaceutical carrier for injection may optionally include a viscosity-enhancing agent (e.g., cellulose derivatives, alginic acid derivatives, dextrans, gelatine, collagen, hyaluronic acids, etc.) preferably type 1 collagen (e.g., CONTIGEN® collagen), the viscosity-enhancing agent included in an amount sufficient to (a) reduce potential leakage of the formulation from the injection site, and/or (b) further treat the incontinence.

The therapeutically effective dosage of any specific compound, the use of which is in the scope of present invention, will vary somewhat from compound to compound, and patient to patient, and will depend upon the condition of the patient and the route of delivery. In general, for intramuscular injection of SDF-1, an amount of from about 10 or 50 micrograms to 400, 800 or 1000 micrograms per injection is appropriate, with each subject receiving one injection into sphincter muscle tissue per treatment session, or a plurality of injections (e.g., 2, 3, 4, 5, 6) into sphincter muscle tissue at different sites therein (e.g., sites distributed circumferentially around the sphincter or sphincter complex at substantially the same depth of insertion into the patient) in each treatment session. Injection may be within the sphincter complex at or adjacent the junction between the smooth muscle and the skeletal muscle.

For the urethral sphincter (or urethral sphincter complex) the injection may be into one or more sites in the external urethral sphincter, and/or one or more sites in the internal urethral sphincter (with the internal urethral sphincter in females being defined as the junction of the bladder neck and the proximal urethra). Administration may by any suitable technique, such as by injection, and when by injection may be carried out by transurethral injection.

For the anal sphincter (or anal sphincter complex) the injection may be into one or more sites in the deep strata and/or superficial strata of the external anal sphincter, and/or one or more sites in the internal anal sphincter. Again administration may be by any suitable technique, such as by injection, and when by injection may be by transrectal injection.

Treatment sessions may be repeated periodically as needed (e.g., once every two or four months). Where a nucleic acid vector is administered, the vector can be administered in an amount effective to achieve corresponding levels of expression of the SDF-1 in the injection site.

The present invention is explained in greater detail in the following non-limiting Examples.

Example 1

In Vivo Evaluation of SDF-1 Administration in Primate Incontinence Model

Methods.

Urinary sphincter deficiency was created in 45 adult female cynomolgus monkeys by selectively cauterizing and then transecting its pudendal innervation. Transaction of the pudendal nerve—the voluntary innervations of the skeletal muscle in the sphincter complex—not only resulted in loss of voluntary nerve innervation to the complex, but deterioration of the skeletal muscle in the sphincter complex, deterioration of the smooth muscle in the sphincter complex, deterioration of vascularization in the sphincter complex, and deterioration of autonomic innervation of smooth muscle in the sphincter complex.

Five million autologous green fluorescence protein (GFP)-labeled skeletal muscle precursor cells were injected into the sphincter complex within 6 weeks post injury in ½ of the monkeys. Additionally, 6 monkeys received sphincteric injections of the chemokine, stromal cell derived factor-1α (SDF-1; also referred to as CXCL-12) (100 μg of SDF-1 with 2.34 mg collagen type 1 in saline for a total of 2 milliliters for injection), or a collagen solution, instead of cells. Maximal urethral pressure (MUP) was measured in all animals at baseline and at 3 and 6 months post sphincteric injections. Urinary sphincters were examined histologically at 3 or 6 months post injection for muscle and collagen content, presence and distribution of injected (GFP+) vs. native cells, presence of vascular structures, somatic and adrenergic innvervation, and cell immunohistochemical phenotype.

Results.

Pudendal nerve transection produced sustained reductions in MUP, sphincteric muscle content, vascularity and innervations over 6 months in the noncell/no CXCL-12 treated monkeys. Both cell and CXCL-12 injections restored these measures to baseline, or those of uninjured control monkeys (FIGS. 1A-1B). All cells within the regenerating sphincter complex of treated animals expressed appropriate muscle-specific proteins (skeletal muscle actin, smoothelin) in the skeletal and smooth muscle layer of the sphincter complex and urothelial cell markers (uroplakins, cytokeratins). Labeled (GFP+) cells could be found incorporating into the skeletal and smooth muscle layers, the vasculature and the urothelium, but only in small numbers (5-10% of the total). There was marked expression of CXCL-12 by injected and native cells within the sphincter complex.

These data show that both injected cells and chemokine produced equal improvements in structure and function in this model of sphincter deficiency.

More particularly, it was observed that SDF-1 injection lead to both improvement of skeletal muscle structure and function and improvement of smooth muscle structure and function, with both occurring in the anatomically correct organization within the sphincter complex of the subject. In addition, SDF-1 injection lead to improvement of vascularization within the sphincter complex, improvement of voluntary innervations (with specificity to skeletal muscle) in the sphincter complex, and improvement of involuntary/autonomic innervations (with specificity to smooth muscle) in the sphincter complex of the subject.

The foregoing is illustrative of the present invention, and is not to be construed as limiting thereof. The invention is defined by the following claims, with equivalents of the claims to be included therein.

What is claimed is:

1. A method of treating a subject afflicted with persistent incontinence, comprising administering stromal cell-derived factor 1 (SDF-1) to a sphincter of the subject in a treatment-effective amount.

2. The method of claim 1, wherein said persistent incontinence is urinary incontinence and the sphincter is the urethral sphincter.

3. The method of claim 1, wherein said persistent incontinence is bowel incontinence and the sphincter is the rectal sphincter.

4. The method of claim 1, wherein said sphincter comprises smooth muscle.

5. The method of claim 1, wherein said sphincter comprises skeletal muscle.

6. The method of claim 1, wherein said sphincter comprises a complex of smooth muscle and skeletal muscle.

7. The method of claim 1, wherein said subject is a male.

8. The method of claim 1, wherein said subject is a female.

9. The method of claim 1, wherein said persistent incontinence comprises urge or latchkey incontinence.

10. The method of claim 1, wherein said administering step is carried out by injecting SDF-1 into said sphincter.

11. The method of claim 10, wherein said injection is by transluminal injection.

12. The method of claim 10, wherein said injection is carried out at a plurality of sites within the sphincter or sphincter complex.

13. The method of claim 1, wherein said SDF-1 is mammalian SDF-1 alpha or mammalian SDF-1 beta.

14. The method of claim 1, wherein said administering step is carried out by injecting a nucleic acid vector encoding SDF-1 into said sphincter, which vector expresses said encoded SDF-1.

15. The method of claim 14, wherein said vector is a plasmid vector and said SDF-1 is mammalian SDF-1 alpha or mammalian SDF-1 beta.

16. The method of claim 1, wherein said subject is afflicted with persistent incontinence persisting at least 3 months.

17. The method of claim 1, wherein said subject is afflicted with persistent incontinence persisting at least 6 months.

18. The method of claim 1, wherein said persistent incontinence comprises deterioration of skeletal muscles, smooth muscle, vascularization, and/or autonomic innervation of the sphincter complex.

* * * * *